United States Patent
Milijasevic

(10) Patent No.: US 9,033,938 B2
(45) Date of Patent: May 19, 2015

(54) CONTROLLED FLOW ADMINISTRATION SET

(75) Inventor: Zoran Milijasevic, Bayview (AU)

(73) Assignee: Acu Rate Pty Limited, Mosman, New South Wales (AU)

( * ) Notice: Subject to any disclaimer, the term of this patent is extended or adjusted under 35 U.S.C. 154(b) by 103 days.

(21) Appl. No.: 12/974,056

(22) Filed: Dec. 21, 2010

(65) Prior Publication Data

US 2011/0127454 A1 Jun. 2, 2011

Related U.S. Application Data

(62) Division of application No. 12/083,042, filed as application No. PCT/AU2006/001465 on Oct. 5, 2006, now Pat. No. 8,870,834.

(30) Foreign Application Priority Data

Oct. 5, 2005 (AU) ................................ 2005905494

(51) Int. Cl.
| | |
|---|---|
| *A61M 5/00* | (2006.01) |
| *A61M 5/168* | (2006.01) |
| *A61M 39/10* | (2006.01) |
| *A61M 5/14* | (2006.01) |

(52) U.S. Cl.
CPC ............ *A61M 5/16877* (2013.01); *A61M 39/10* (2013.01); *A61M 2005/1402* (2013.01); *A61M 2205/6081* (2013.01)

(58) Field of Classification Search
CPC ............. F16K 5/12; F16K 3/08; F16K 3/085; F16K 3/32; A61M 5/141; A61M 5/16877; A61M 5/16881; A61M 2205/0244; A61M 16/20; A61M 39/10; A61M 5/168; A61M 5/365; A61M 5/16886; A61M 39/22; A61M 2039/2433; A61M 2039/2446; A61M 2005/1402; A61M 2205/6081; F15D 1/02; F15D 1/00
USPC ........ 138/42–43; 604/30, 251–252, 248, 246; 251/205
See application file for complete search history.

(56) References Cited

U.S. PATENT DOCUMENTS

| | | | | | |
|---|---|---|---|---|---|
| 1,964,300 | A | * | 6/1934 | Perry et al. ...................... | 138/43 |
| 2,236,084 | A | * | 3/1941 | Brown ............................ | 138/43 |
| 2,765,809 | A | * | 10/1956 | Lamar ........................ | 137/625.12 |
| 3,532,126 | A | * | 10/1970 | Boothe ........................... | 138/43 |
| 3,532,127 | A | * | 10/1970 | Bottone, Jr. et al. ............ | 138/43 |
| 3,665,965 | A | * | 5/1972 | Baumann ........................ | 138/42 |

(Continued)

OTHER PUBLICATIONS

U.S. Patent and Trademark Office, Non-Final Office Action, mailed Feb. 2, 2011, U.S. Appl. No. 12/083,043, filed Apr. 3, 2009, Zoran Milijasevic.

(Continued)

*Primary Examiner* — Jason Flick
(74) *Attorney, Agent, or Firm* — Nelson Mullins Riley & Scarborough, LLP

(57) ABSTRACT

A flow control device includes a connector defining a first receiving formation for receiving a first conduit, a second receiving formation for receiving a second conduit and a cross member separating the first receiving formation and the second receiving formation. An orifice plate is received in the cross member to control flow of fluid, in use, through the conduits received in the first and the second receiving formations of the connector, the orifice plate defining at least one substantially frustoconical orifice.

8 Claims, 8 Drawing Sheets

(56) References Cited

U.S. PATENT DOCUMENTS

| | | | |
|---|---|---|---|
| 4,011,893 A * | 3/1977 | Bentley | 138/43 |
| 4,079,737 A * | 3/1978 | Miller | 604/248 |
| 4,822,344 A * | 4/1989 | O'Boyle | 604/248 |
| 4,917,687 A * | 4/1990 | O'Boyle | 604/248 |
| 5,009,251 A * | 4/1991 | Pike et al. | 137/599.06 |
| 5,014,750 A * | 5/1991 | Winchell et al. | 138/43 |
| 5,315,859 A * | 5/1994 | Schommer | 73/1.25 |
| 5,409,477 A * | 4/1995 | Caron et al. | 604/407 |
| 5,449,350 A * | 9/1995 | Lasaitis et al. | 604/246 |
| 5,489,265 A * | 2/1996 | Montalvo et al. | 604/67 |
| 5,499,968 A * | 3/1996 | Milijasevic et al. | 604/30 |
| 6,647,983 B2 * | 11/2003 | Smith et al. | 128/205.24 |
| 7,487,800 B2 | 2/2009 | Lammers | |
| 2002/0029577 A1 * | 3/2002 | Wightman | 62/222 |
| 2005/0092002 A1 * | 5/2005 | Wightman | 62/222 |

OTHER PUBLICATIONS

U.S. Patent and Trademark Office, Final Office Action, mailed Aug. 17, 2011, U.S. Appl. No. 12/083,042, filed Apr. 3, 2009, Zoran Milijasevic.

Amendment filed with the U.S. Patent and Trademark Office in Response to the outstanding Office Action, mailed Feb. 2, 2011, U.S. Appl. No. 12/083,042, filed Apr. 3, 2009, Zoran Milijasevic.

* cited by examiner

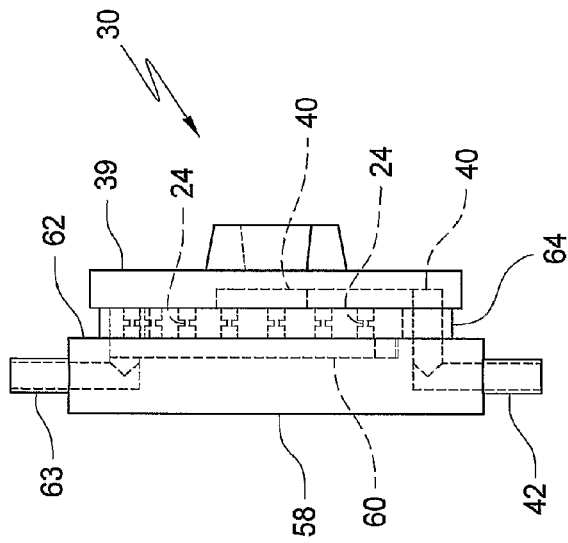
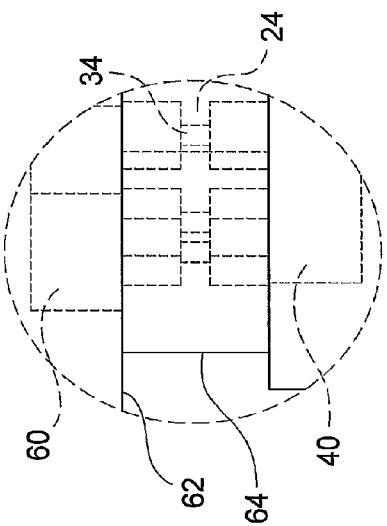
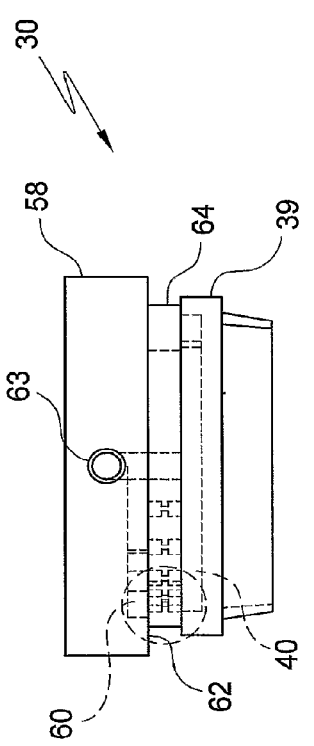
Fig. 5
Fig. 6
Fig. 7

CONTROLLED FLOW ADMINISTRATION SET

The present application claims the priority benefit of and incorporates herein by reference, in their entireties, the disclosures of U.S. patent application Ser. No. 12/083,042, filed Apr. 3, 2009, International Application No.: PCT/AU2006/001465, filed Oct. 5, 2006, which designated the United States of America, and Australian Provisional Patent Application No. 2005905494 filed on Oct. 5, 2005.

FIELD OF THE INVENTION

This invention relates to a flow control device. More particularly, the invention relates to a flow control device particularly, but not necessarily exclusively, for use in an intravenous (IV) administration set, to an orifice plate for a flow control device and to a component for an IV administration set.

BACKGROUND OF THE INVENTION

At present, infusion of fluids into a patient is managed by medical personnel. Fluids are infused parenterally into a patient for a variety of reasons. It is often critical that the fluid being administered is infused into the patient's body in the required doses and flow rates.

This is usually done either manually using a roller clamp or automatically using an infusion pump. Manual roller clamps are inaccurate and are difficult to set to maintain an accurate flow rate. In addition, when applied to a length of plastics conduit, the plastics conduit itself may, in due course, plastically deform resulting in a loss of clamping action of the roller clamp. This could have the potentially serious consequences of an unregulated supply of fluid into the patient's body.

Infusion pumps, while maintaining an accurate flow rate, are expensive items. In addition, because an infusion pump is an electromechanical device, there is a risk of failure of the infusion pump which, once again, has potentially extremely serious consequences. Further, with the increasing age of the population there is more pressure for bed places in hospitals resulting in an increasing homecare market. Providing homecare patients with infusion pumps is expensive and has attendant risks as well. In addition, in large parts of the world, there are insufficient funds to make infusion pumps available to patients, whether in hospitals or in homecare.

Also, in the case of roller clamps, there is a continuous need for vigilance by medical personnel to ensure that the fluid is being infused at the desired flow rate. Often, in parts of the world, medical personnel are in short supply and are unable to provide the requisite duty of care.

A need therefore exists for a device which requires minimal human intervention, is not able to be tampered with, whether by the patient or by medical personnel, and which requires very little, if any, training or supervision to use.

SUMMARY OF THE INVENTION

According to a first aspect of the invention, there is provided a flow control device which includes a connector defining a first receiving formation for receiving a first conduit, a second receiving formation for receiving a second conduit and a cross member separating the first receiving formation and the second receiving formation; and an orifice plate received in the cross member to control flow of fluid, in use, through the conduits received in the first and the second receiving formations of the connector, the orifice plate defining at least one substantially frustoconical orifice.

It will be appreciated that, with this configuration of connector, there is a chamberless communication between the ends of the conduit and the orifice plate. Thus there is no chamber in which air bubbles can form which could inhibit proper operation of the flow control device.

Further, while a single orifice in the device should normally provide sufficiently accurate metering of flow rate, it may be necessary, where greater accuracy is required, to use a plurality of smaller orifices in parallel. In general, each orifice has an accuracy of +/−3%. It will be appreciated that, if a plurality of orifices are used together, the worst case scenario would be an inaccuracy in the flow rate of +3% or −3%. The likelihood, however, is that there would be an averaging out of inaccuracies over the orifices resulting in an overall greater accuracy of flow rate over all the orifices. Hence, there may be circumstances where the orifice plate comprises a plurality of orifices.

The connector may comprise a cylindrical housing defining a pair of opposed sockets, the sockets forming the receiving formations with a transversely extending web defining the cross member. At least the web may be of a resiliently flexible material. Preferably, the housing is a one-piece unit of a resiliently flexible material such as a polymeric or elastomeric material which facilitates lateral deformation of the housing for priming purposes, i.e to prime a system, such as an IV set, with which the flow control device is used.

The orifice plate may be of a rigid material, such as a metal or a suitably rigid plastics material. Preferably, the orifice is formed in the plate by laser drilling. Laser drilling enables an orifice of sufficiently accurate dimensions to be formed. It will, however, be appreciated that the orifice plate could be of a flexible material, such as a polymeric material. Further, although laser drilling is the preferred form of forming the orifice, the orifice could be formed in other ways such as, for example, by mechanical drilling, chemical forming, using ultraviolet radiation, or the like.

For any given angle of frustum of the orifice, flow rate through the orifice may be directly proportional to a cross-sectional area of a smaller opening of the orifice. Flow rate through the orifice may be governed by a linear relationship of the form:

$$y = mx \pm c$$

where:

y is flow rate in ml/hr;

x is cross-sectional area of the smaller end of orifice in microns$^2$; and m and c are constants governed by the angle of the frustum.

The angle of frustum of the orifice may be in the range of about 15° to 50°, more particularly, in the range of about 20° to 28° and, optimally, about 24°.

The orifice may have a diameter (as measured at its smaller opening) in the range from about 1 to about 700 microns, more particularly about 30 to about 700 microns. Further, the orifice may have an aspect ratio, being defined as the ratio between a length of the orifice and its diameter, which is less than or equal to 10 and, preferably, about 2.

The connector may be of a coloured material. More particularly, the connector may be colour coded with each colour being associated with a particular flow rate.

According to a second aspect of the invention, there is provided a flow control device which includes a connector defining a first receiving formation for receiving a first conduit, a second receiving formation for receiving a second conduit and a cross member separating the first receiving formation and the second receiving formation, the connector being a one-piece unit of a resiliently flexible material which facilitates lateral deformation of the connector for priming purposes; and an orifice plate, defining at least one orifice, received in the cross member to control flow of fluid, in use, through the conduits received in the first and the second receiving formations of the connector.

Once again, the orifice plate may be a rigid member received in the cross member, lateral deformation of the connector causing the formation of priming ports between the orifice plate and the cross member.

The connector may comprise a cylindrical housing defining a pair of opposed sockets, the sockets forming the receiving formations with a transversely extending web defining the cross member.

The orifice plate may be of a rigid material. Preferably, the orifice is formed in the plate by laser drilling.

The orifice may be a frustoconical orifice and, for any given angle of frustum of the orifice, flow rate through the orifice is directly proportional to a cross-sectional area of a smaller opening of the orifice.

The connector may be of a coloured material. More particularly, the connector may be colour coded with each colour being associated with a particular flow rate.

According to a third aspect of the invention, there is provided an adjustable flow rate flow control device which includes a fluid delivery arrangement having an inlet and defining a plurality of spaced orifices in communication with the inlet; and a passage defining member displaceably arranged relative to the delivery arrangement, the passage defining member defining a passage which is able to be brought into flow communication with a desired number of orifices to achieve a desired flow rate through the outlet by adjusting the position of the passage defining member relative to the delivery arrangement; and an outlet in communication with the passage of the passage defining member.

The device may include a supply duct in flow communication with the passage defining member.

The fluid delivery arrangement may include a housing defining a first flow path, the passage of the passage defining member defining a second flow path. Further, the fluid delivery arrangement may include a separating element separating the first flow path from the second flow path, the separating element having the orifices.

The separating element may be a gasket of a resiliently flexible material, the gasket defining the orifices. The orifices may be defined in the gasket by a plurality of rigid orifice plates, each orifice plate defining at least one orifice.

In one embodiment, the passage defining member may include a rotary actuator which is rotatably arranged relative to the housing, the passage being defined in a body of the rotary actuator. The outlet may be defined in the housing and the gasket may have an opening defined through it in alignment with the outlet so that fluid that has passed through the orifices is able to flow out through the outlet via the passage of the passage defining member.

In another embodiment, the supply duct may constitute the passage defining member, the supply duct being slidably arranged relative to the delivery arrangement to bring the desired number of orifices into fluid communication with the passage.

Each orifice may be formed by laser drilling. Laser drilling enables an orifice of sufficiently accurate dimensions to be formed.

Each orifice may be a frustoconical orifice having the features and characteristics described above with reference to the first aspect of the invention.

According to a fourth aspect of the invention, there is provided a component for an intravenous (IV) set, the component including a conduit of a silicone material.

The silicone material may be reinforced to inhibit kinking and to enhance the elasticity of the conduit. The reinforcing may be a helically wound reinforcing member carried in a wall of the conduit. The reinforcing member may be selected from the group consisting of a plastics material, such as nylon, a metal material, such as stainless steel, and a shape memory alloy.

The component may include a flow control device for interconnecting two lengths of conduit, the flow control device being as described above with reference to either the first aspect of the invention or the second aspect of the invention, the connector of the flow control device being of a silicone material. Instead, the component may include a flow control device for interconnecting two lengths of conduit, the flow control device being as described above with reference to the third aspect of the invention, at least one of the passage defining member and the supply duct being of a silicone material.

According to a fifth aspect of the invention, there is provided a component for an intravenous (IV) set, the component including a conduit of a reinforced polymeric material.

The reinforcing may be a helically wound reinforcing member carried in a wall of the conduit. The reinforcing member may be selected from the group consisting of a plastics material, such as nylon, a metal material, such as stainless steel, and a shape memory alloy.

BRIEF DESCRIPTION OF THE DRAWINGS

FIG. 5 shows a front view of a further embodiment of an adjustable flow rate flow control device;

FIG. 6 shows a side view of the device of FIG. 5;

FIG. 7 shows a plan view of the device of FIG. 5;

DETAILED DESCRIPTION OF THE EXEMPLARY EMBODIMENTS

Figure 1:
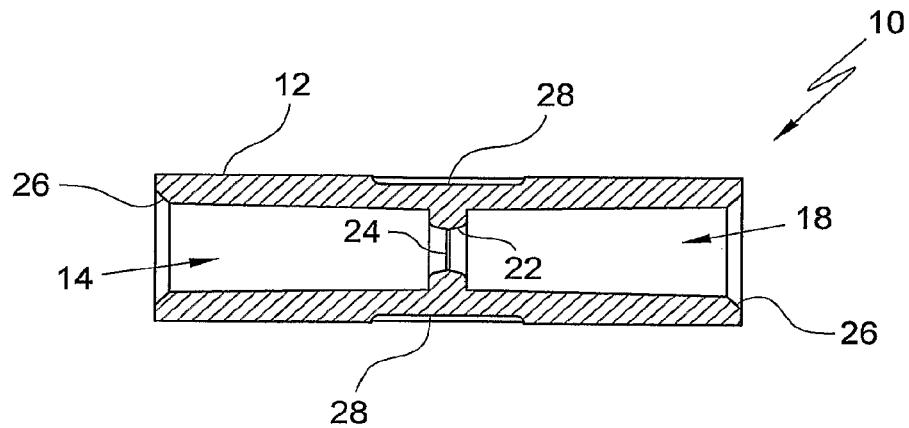
FIG. 1 shows a sectional side view of a flow control device in accordance with an embodiment of a first aspect of the invention.
Figure 2:
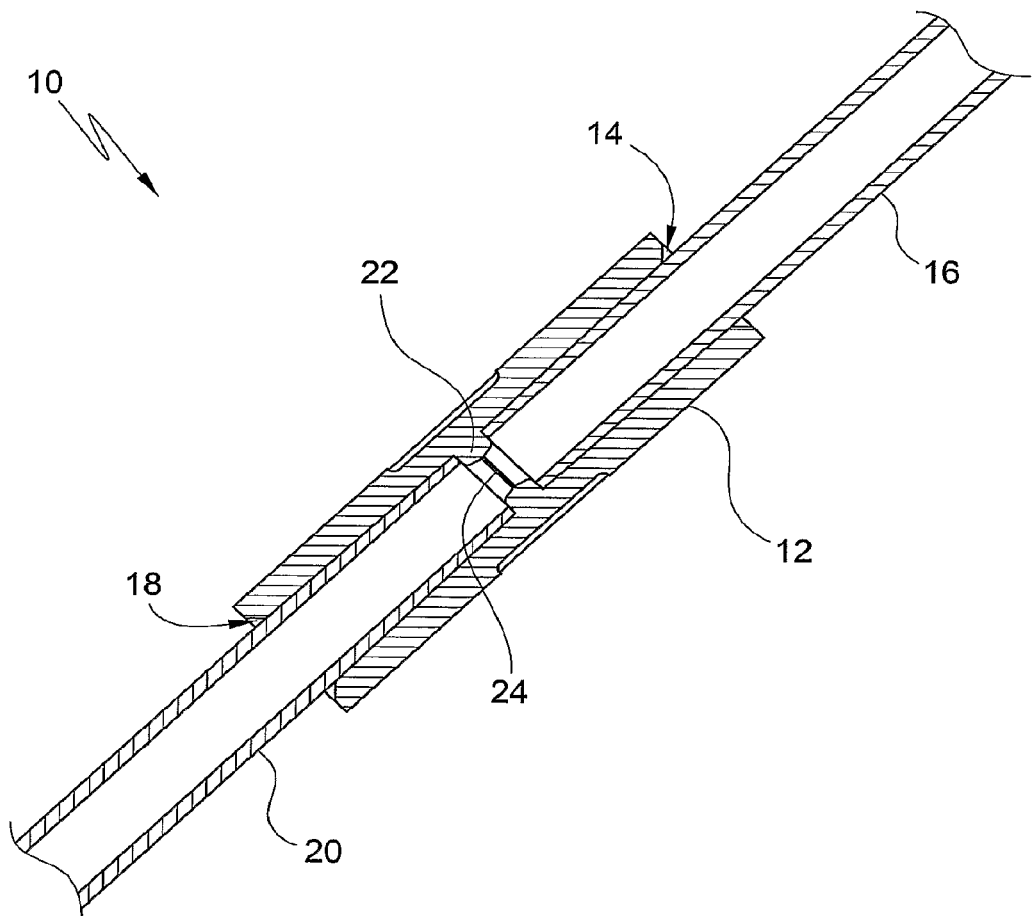
FIG. 2 shows a sectional side view of the flow control device of FIG. 1, in use.

Referring initially to FIGS. 1 and 2 of the drawings, an embodiment of a flow control device is designated generally by the reference numeral 10. The flow control device 10 comprises a connector in the form of a housing 12. The housing 12 defines a first receiving formation 14 in which a first conduit 16 (FIG. 2) is received and a second receiving formation 18, spaced from the first receiving formation 14, in which a second conduit 20 is received. The receiving formations 14 and 18 are arranged on opposed sides of a cross member, or web, 22. The web 22 supports an orifice plate 24, the orifice plate 24 being a separate component and defining a frustoconical orifice 34 which will be described in greater detail below.

The housing 12 is of a resiliently flexible material. The housing 12 is of a polymeric material or, instead, is of an elastomeric material, more particularly, a silicone material.

It will be noted that each receiving formation 14, 18 is slightly tapered to facilitate a snug fit of the conduits 16, 20 in the receiving formations 14, 18 respectively and to impose a clamping-like action on the conduits 16 and 20 to retain them in their respective receiving formations 14, 18. It will also be noted that an end of each conduit 16, 20 butts up against the web 22 so that there is chamberless communication between the conduits 16, 20 and the orifice 34.

To facilitate insertion of the conduits 16, 20 into their associated receiving formations 14, 18, an access opening of each receiving formation 14, 18 has a chamfered edge 26.

As described above, the housing 12 is of a resiliently flexible material. It will be appreciated that the orifice plate 24 has very small dimensions measured on the micron scale. It is necessary to prime a system with which the flow control device 10 is used to effect fluid flow through the orifice plate 24.

For this purpose, the housing 12 includes a pair of opposed finger pads 28 arranged diametrically opposite each other at the web 22 of the housing 12. When pressure is applied to the housing 12 via the finger pads 28, the housing deforms laterally and adopts an elliptical shape creating a pair of opposed ports on either side of the orifice plate 24 through which fluid can flow bypassing the orifice of the orifice plate 24 to commence fluid flow in the flow control device 10. Thus, a simple priming action is provided by the flow control device 10.

In addition, as shown in FIG. 2 of the drawings, due to the construction of the substantially H-shaped housing 12, no chambers are defined in the housing 12 thereby minimising the likelihood of air bubble entrapment. Once again, it will be appreciated that air bubble entrapment can be a significant impediment when considering the size of the orifice 34 of the orifice plate 24.

The flow control devices 10 may be made available with housings 12 of various colours. The flow control devices 10 are therefore colour coded with the colours of the housings 12 being representative of particular flow rates provided by the orifice plate 24 of the relevant flow control devices 10. Thus, personnel can be trained to select the correct flow control device 10 for a particular application merely by learning the different colours associated with the different flow rates.

The device 10 described with reference to FIGS. 1 and 2 of the drawings is a single flow rate device. Should it be desired, using the single flow rate device 10, to change the flow rate of equipment with which the flow control device 10 is used, it is necessary to remove the selected flow control device 10 from between the conduit 16, 20 and to interpose a new flow control device, having a different orifice plate 24 and, hence, flow rate, between the conduits 16, 20.

FIGS. 3 to 9 of the drawings show embodiments of flow control devices having adjustable flow rates.

Figure 3:
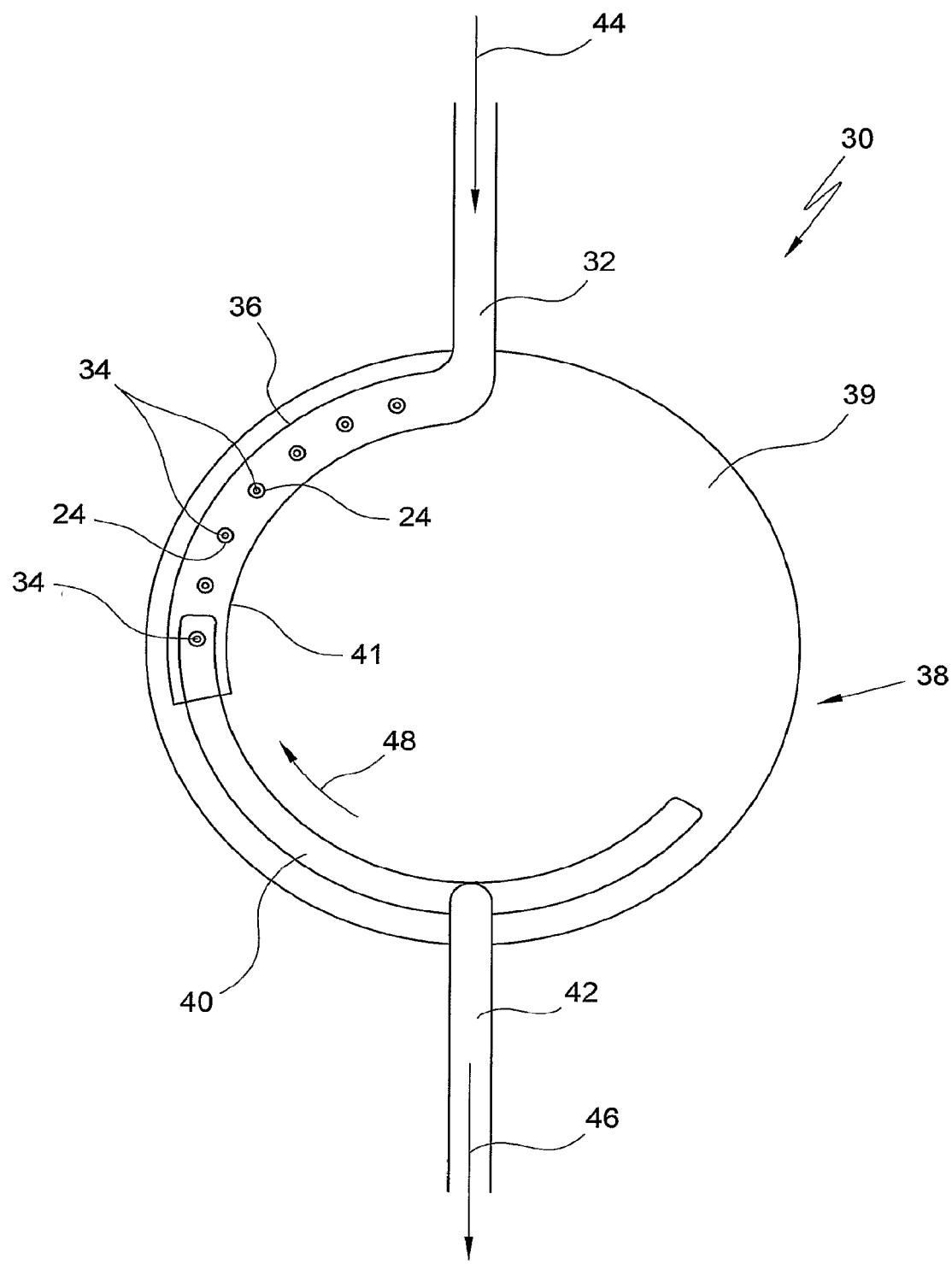
FIG. 3 shows a schematic, sectional side view of an adjustable flow rate flow control device in accordance with a first embodiment of a second aspect of the invention.

In FIG. 3 of the drawings, the flow control device is designated generally by the reference numeral 30. The flow control device 30 includes a delivery arrangement, or duct, 32 for delivering fluid to be infused from a container of the fluid. A plurality of spaced orifices 34 are defined in a wall 36 of the delivery duct 32. Each orifice 34 is defined by an orifice plate 24 of the type used in the single flow rate flow control device 10, the orifice 34 being described in greater detail below.

A passage defining member 38 is displaceably arranged relative to the delivery duct 32. In the embodiment illustrated in FIG. 3 of the drawings, the passage defining member 38 is a rotary actuator 39 defining an arcuate passage or channel 40 which cooperates with a correspondingly arcuate portion 41 of the delivery duct 32.

A supply duct 42 is in fluid flow communication with the passage 40 and supplies fluid from the flow control device 30 to a patient.

In use, fluid is delivered, as illustrated by arrow 44, via the delivery duct 32 and through at least one of the orifices 34 into the passage 40. Fluid flows from the passage 40, under gravity, through the supply duct 42 as illustrated by the arrow 46.

To adjust or vary the flow rate of fluid in the supply conduit 42, the rotary actuator 39 is rotated relative to the delivery duct 32 so that the desired number of orifices 34 are brought into fluid flow communication with the passage 40. As more orifices 34 come into register with the passage 40, the flow rate through the flow control device 30 increases and vice versa.

Figure 4:
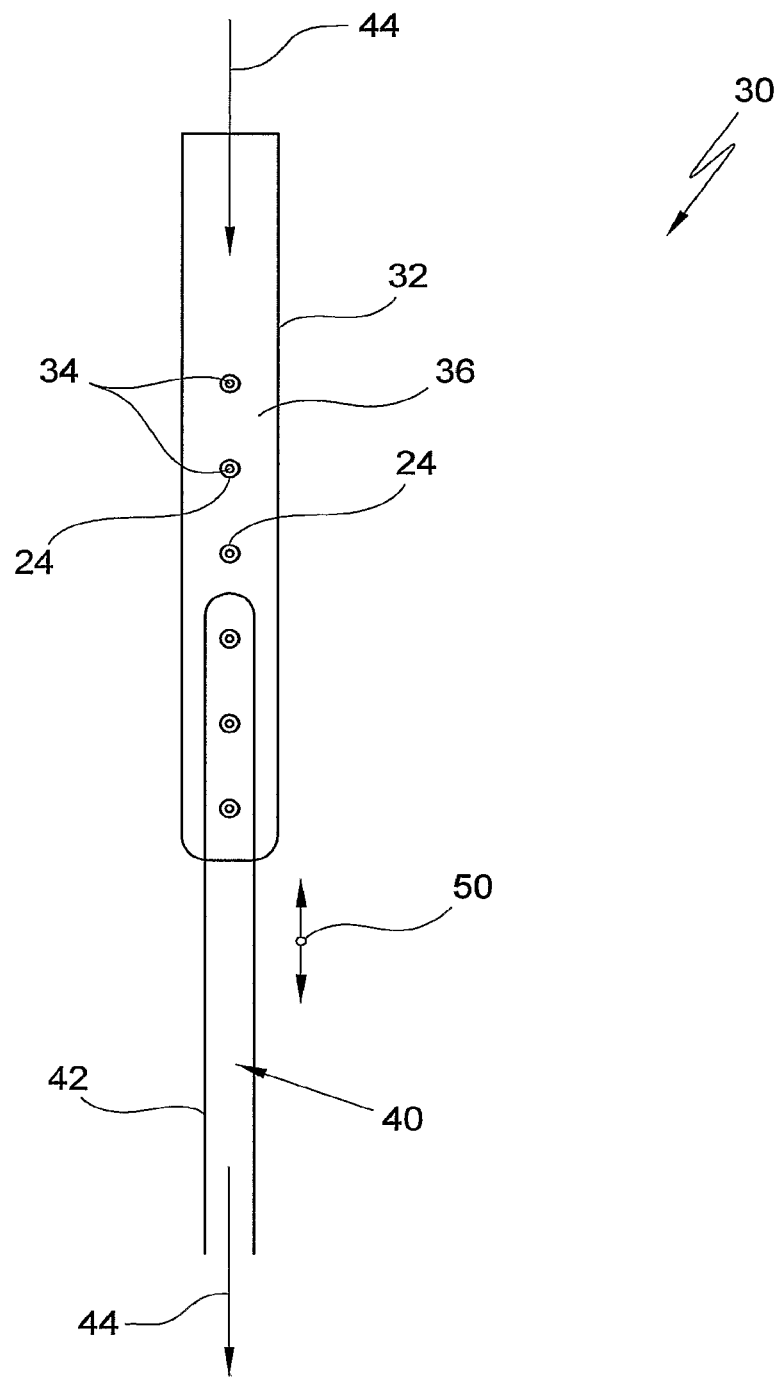
FIG. 4 shows a schematic, sectional side view of an adjustable flow rate flow control device in accordance with a second embodiment of the second aspect of the invention.

In FIG. 4 of the drawings, another embodiment of an adjustable flow rate flow control device is illustrated. With reference to FIG. 3 of the drawings, like reference numerals refer to like parts, unless otherwise specified.

In this embodiment, the supply duct 42 is telescopically received within the delivery duct 32. By displacing the supply duct 42 relative to the delivery duct 32 in the direction of arrows 50, a greater or fewer number of orifices 34 is brought into communication with the passage 40. In this embodiment, the supply duct 42 itself forms the passage defining member.

In both embodiments, the conduit 16 attaches to the delivery duct 32 and the conduit 20 attaches to the supply duct 42, spigot-socket fashion. Instead, the delivery duct 32 and the supply duct 42 may function as the conduits 16, 20 respectively.

Further, in both embodiments, to prime the flow control device 30, at least the supply duct 42 is of a resiliently flexible material so that a pumping action effected laterally on a wall of the supply duct 42 effects priming of the device 30. In the case of the embodiment of FIG. 3, the rotary actuator 39 may, in addition or instead, be of a resiliently flexible material to effect priming by laterally deforming a wall of the actuator defining the passage 40.

Instead, to effect priming, at least one of the orifices 34 is not defined by an orifice plate 24 but, rather, is constituted by an opening which allows priming. Once flow has commenced, this opening is closed off. The priming may be self-closing, eg. by being spring-loaded.

Referring now to FIGS. 5 to 8 of the drawings, a further embodiment of a rotary adjustable flow rate flow control device 30 is illustrated. With reference to FIGS. 3 and 4 of the drawings, like reference numerals refer to like parts, unless otherwise specified.

In this embodiment, the delivery arrangement 32 includes a housing 58 defining a first flow path in the form of an arcuate channel 60 in a surface 62 of the housing 58. The channel 60 communicates with an inlet 63 of the housing 58. The conduit 16, in use, is attached to the inlet 63.

The device 30 includes the rotary actuator 39 separated from the surface 62 of the housing 58 by a separating element in the form of a gasket 64. The rotary actuator 39 defines the arcuate passage or channel 40 which forms a second flow path.

The gasket 64 carries a plurality of spaced orifice plates 24 each defining at least one orifice 34. As described above with reference to FIG. 3 of the drawings, as the rotary actuator 39 is rotated, a greater or fewer number of orifices 34 is brought into communication with the channel 40.

Figure 8:
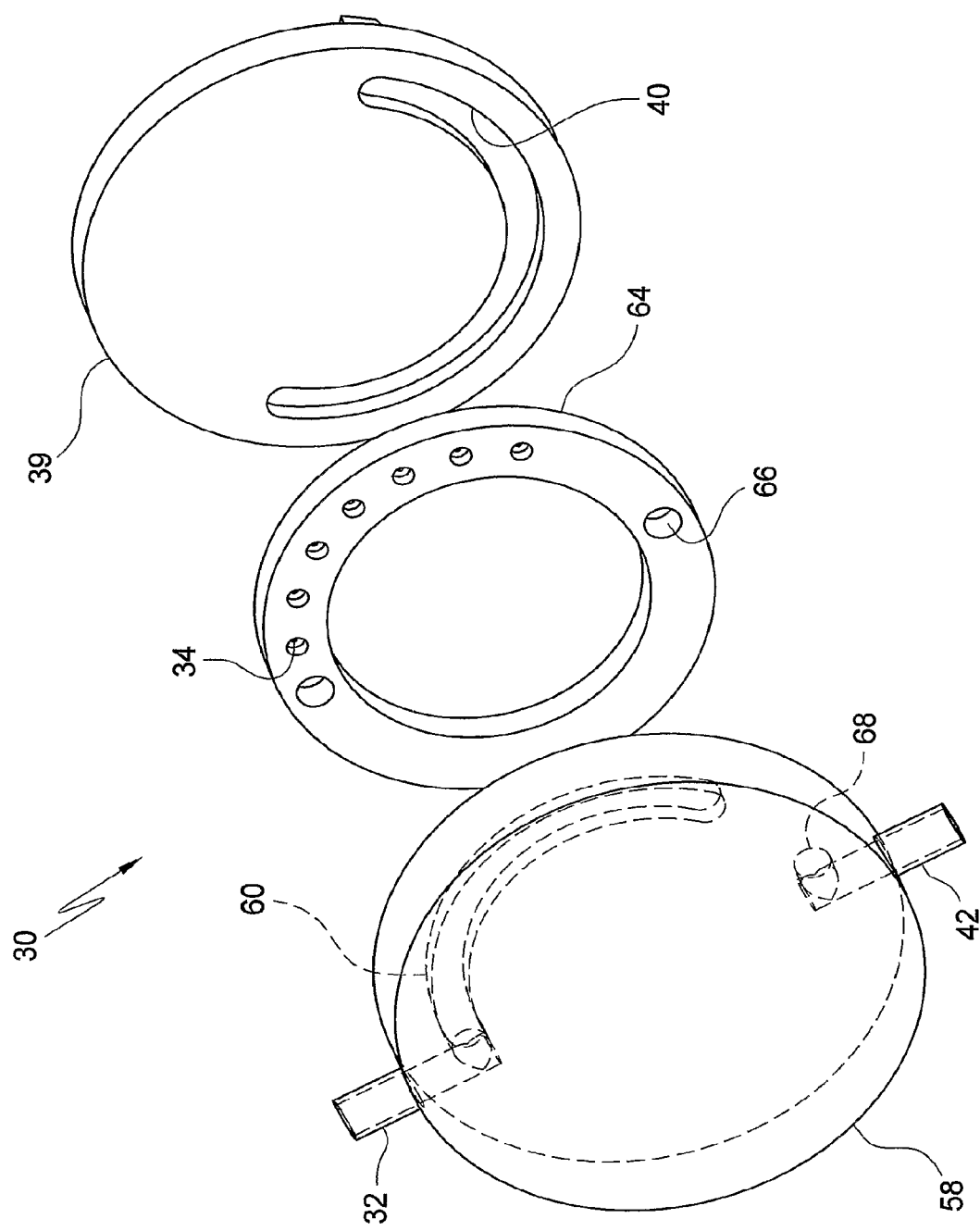
FIG. 8 shows a three dimensional, exploded view from the rear of the device of FIG. 5.

As shown more clearly in FIG. 8 of the drawings, the gasket 64 defines an opening 66 which is in register with an outlet 68 defined in the housing. The opening 66, in turn, communicates with the arcuate passage 40 to enable fluid, which has passed from the first flow path through the orifices 34 of the orifice plates 24 into the second flow path to exit the flow control device 30 through the outlet 68 into the supply duct 42. Once again, the conduit 20 is, in use, connected to the supply duct 42.

Figure 9:
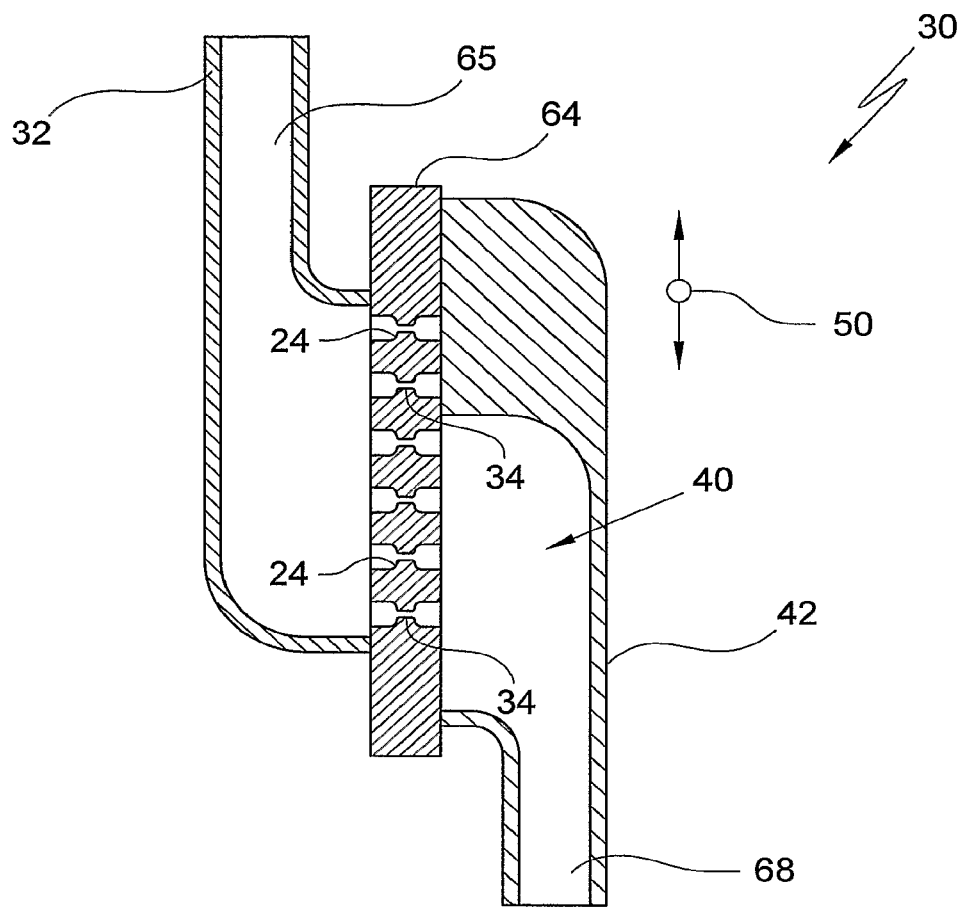
FIG. 9 shows a schematic sectional side view of another embodiment of an adjustable flow rate flow control device.
Figure 10:
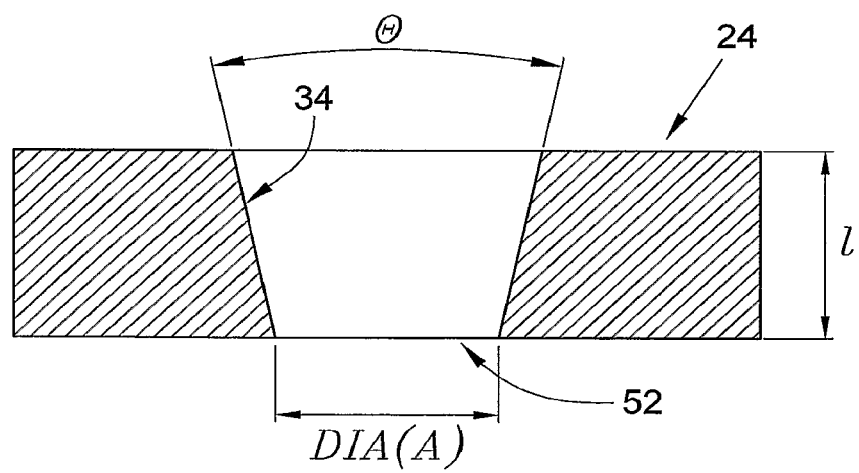
FIG. 10 shows a sectional side view of an embodiment of an orifice plate, in accordance with another aspect of the invention, for use with the devices of FIGS. 1-9.
Figure 11:
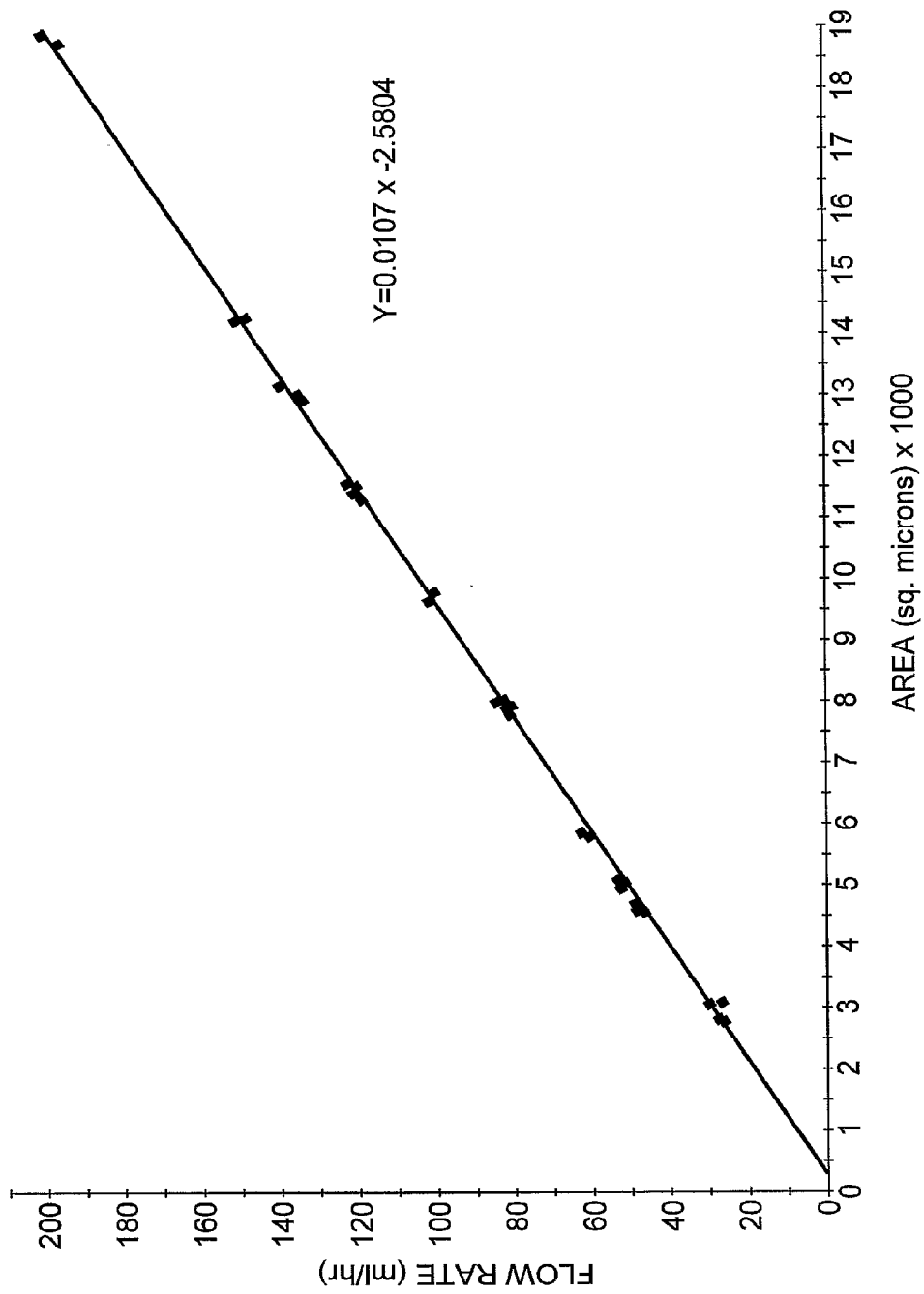
FIG. 11 shows a graph of flow rate vs. cross-sectional area for the orifice plate of FIG. 10.
Figure 12:
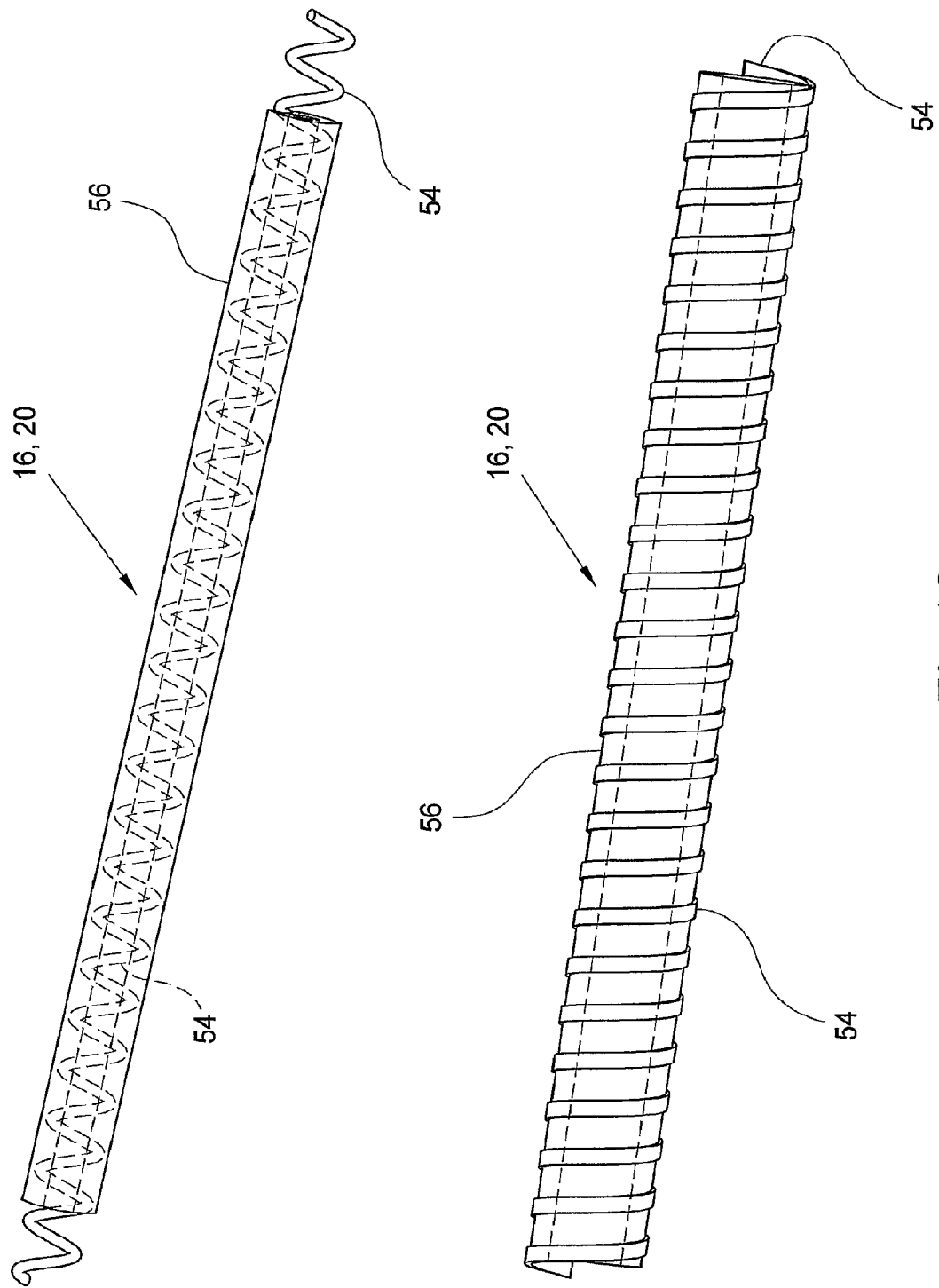
FIG. 12 shows two variations of a component for an IV set in accordance with further aspects of the invention.

Referring now to FIG. 9 of the drawings, a further embodiment of a linearly adjustable flow rate flow control device is illustrated. Once again, with reference to FIGS. 3 to 8 of the drawings, like reference numerals refer to like parts, unless otherwise specified. In this embodiment, the delivery arrangement or duct 32 defines an inlet 65. The inlet 65 is in flow communication with orifice plates 24 carried by the gasket 64 via a the first flow path defined by the duct 32.

The supply duct 42 is arranged on an opposed side of the gasket 64 and has the passage 40 in flow communication with the orifice plates 24.

By slidably displacing the supply conduit 42 in the direction of arrows 50 the desired number of orifices 34 can be brought into communication with the passage 40 of the duct 42 to be fed, through an outlet 68, which is an exit aperture of the supply conduit 42, to the conduit 20, connected, in use, to the supply duct 42, for infusion into a patient.

In all the embodiments above with respect to the adjustable flow rate flow control devices 30, the rotary actuator 39 or the supply duct 42, as the case may be, is attached by a ratchet like mechanism. As a result when the rotary actuator 39 or the supply duct 42 is displaced, an audible click is heard by the user as each orifice 34 is exposed or occluded, as the case may be, so that the user knows how many orifices 34 are open or closed.

In the application of the flow control device 10, 30 in an intravenous (IV) administration set, the flow control device 10, 30 is arranged between the two conduits 16, 20. The conduit 16 leads from a drip counter (not shown) of a container (also not shown) of fluid to be infused. The container may either be a flexible or a rigid container. The conduit 20 has a Luer attached to its end opposite the end attached to the flow control device 10, 30 for enabling parenteral infusion of fluids into the patient to be effected.

When such an IV set is used with the flow control device 10, 30 the flow rate is governed by a number of factors. These factors include the pressure head developed as a result of gravitational feed of the fluid. Thus, the container of fluid is, in use, arranged at an elevated position relative to the patient. Further, the flow rate is dependent on the viscosity of the fluid and, thirdly, the degree of back pressure occurring as the fluid enters the patient.

Insofar as viscosity is concerned, temperature changes can cause a great variance in viscosity. With a manual roller clamp of the type presently in use, this can result in dramatic differences in the flow rate of fluid in the IV set.

The orifice plate 24 used with the single flow rate flow control device 10 or defining the orifices 34 of the variable flow rate flow devices 30, as the case may be, has a frustoconical orifice 34. The frustoconical orifice 34 is formed by laser drilling in the orifice plate 24. In forming the orifice 34 by laser drilling, the size of the hole is measured in real time while being drilled to stop drilling when an outlet opening 52 is of the required cross sectional area. Generally, the outlet opening 52, being the smaller end of the frustum, is circular but circularity of the outlet opening 52 is not critical. What is of greater relevance is the angle, $\theta$, and the cross sectional area, A, of the outlet opening 52 of the orifice 34.

The Applicants have found that, with a constant angle, $\theta$, a linear variation in flow rate for a varying cross sectional area A is achieved. This is shown in greater detail in FIG. 6 of the drawings where it is shown that the relationship between cross sectional area and flow rate is governed by an equation of the form:—

$$y = mx \pm c. \qquad \text{Equation 1}$$

where:
y=flow rate in ml/hr;
x=cross-sectional area, A, of the orifice 34; and
m and c are constants governed by the angle of the frustum of the orifice 34.

For an angle $\theta$ of approximately 24°, the equation is y=0.0107x−2.5804.

The orifice 34 has a length, l, in the range of 60 to 90 μm, more particularly, about 70 to 80 μm and, optimally, about 75 μm. The orifice 34 has an aspect ratio, being defined as the ratio between the length, l, and the diameter of the opening 52, which is less than or equal to 10 and, preferably, about 2.

The orifice plate 24 is of a suitable metal or rigid plastics material which, as indicated above, is laser drilled to form the orifice 34.

Flow rate through the orifice is governed by the following equation:—

$$\text{Flowrate} = A\sqrt{P/\rho} \qquad \text{Equation 2}$$

where:
A=cross sectional area of the orifice 34;
P=pressure drop across the orifice 34; and
$\rho$=density of the fluid.

It will therefore be noted that with the use of the orifice 34 of the type described above, flow rate is independent of viscosity and is proportional to the square root of the pressure drop across the orifice 34. Thus, with the use of such a flow control device 10, 30, a more accurate, constant flow rate can be achieved and variations in viscosity of the fluid do not affect the flow rate through the orifice 34 to any significant extent.

The conduits 16, 20, as well as the housing 12 of the flow control device 10, may be of a polymeric material. Instead, these components may be of a synthetic elastomeric material, more particularly, a silicone material. To inhibit kinking and to improve the elasticity at least of the conduits 16, 20, the conduits 16, 20 are reinforced with a reinforcing member 54. The reinforcing member 54 is a helical element at least partially embedded in a wall 56 of the conduits 16, 20. The reinforcing member 54 is either of a suitable metal material, such as stainless steel, nickel-titanium alloy, or the like or, instead, the reinforcing member 54 is of a suitable plastics material, such as nylon. With the provision of the reinforcing member 54, kinking of the conduit 16, 20, is inhibited and, counter-intuitively, such conduits 16, 20, work more efficiently with conventional manual roller clamps as well.

It is an advantage of at least the preferred embodiments of the flow control devices 10, 30 that they do not have chambers in which air can be trapped preventing the flow of fluid through the IV set with which that flow control device 10, 30 is used. In addition, a flow control device 10, 30 is provided which is able to maintain a constant flow rate more accurately than other non-electromechanical devices of which the Applicants are aware. The flow control devices 10, 30 do not require any specialist training for use nor do they require continuous monitoring by medical personnel.

Further, where the conduits 16, 20 are of a silicone material it makes them easy to join to other silicone components by use of a silicone adhesive and, for joining to non-elastomeric components, are able to seal with the use of sealing rings, etc.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An intravenous administration set adjustable flow rate flow control device which includes
    an intravenous fluid delivery arrangement having an inlet and a plurality of spaced orifice plates, each defining an orifice configured to deliver a metered quantity of intravenous fluid, all of the orifices being simultaneously in fluid flow communication with the inlet via a single conduit, the fluid delivery arrangement including a separating element, comprising gasket of a resiliently flexible material, with the gasket carrying the orifice plates; and
    a passage defining member displaceably arranged relative to the delivery arrangement downstream of the orifices, the passage defining member defining a passage which is able to be brought into direct fluid flow communication with a desired number of orifices to achieve a desired flow rate through an outlet, which is in communication with the passage of the passage defining member, by adjusting the position of the passage defining member relative to the orifices of the delivery arrangement, the flow rate through the outlet being dependent on the number of orifices in direct communication with the passage of the passage defining member.

2. The device of claim 1 which includes a supply duct in flow communication with the passage defining member.

3. The device of claim 1 in which the fluid delivery arrangement includes a housing defining the single conduit, the single conduit comprising a first flow path, with the passage of the passage defining member defining a second flow path.

4. The device of claim 3 in which the separating element separates the first flow path from the second flow path.

5. The device of claim 1 in which the gasket defines a plurality of openings with each opening of the gasket having one of the orifice plates received in it.

6. The device of claim 5 in which the outlet is defined in the housing and in which the gasket has an opening defined through it in alignment with the outlet so that fluid that has passed through the orifices is able to flow out through the outlet via the passage of the passage defining member.

7. The device of claim 5 in which the passage defining member includes a rotary actuator which is rotatably arranged relative to the housing, the passage being defined in a body of the rotary actuator.

8. The device of claim 2 in which the supply duct constitutes the passage defining member, the supply duct being slidably arranged relative to the delivery arrangement to bring the desired number of orifices into fluid communication with the passage.

* * * * *